US012625142B2

(12) United States Patent
Arsenjans et al.

(10) Patent No.: US 12,625,142 B2
(45) **Date of Patent: *May 12, 2026**

(54) ASSAY FOR MEASURING BINDING AFFINITY FOR CARDIOLIPIN OF BIOLOGICALLY ACTIVE COMPOUNDS

(71) Applicant: Latvian Institute of Organic Synthesis, Riga (LV)

(72) Inventors: Pavels Arsenjans, Riga (LV); Pavels Dimitrijevs, Daugavpils (LV)

(73) Assignee: Latvian Institute of Organic Synthesis, Riga (LV)

( * ) Notice: Subject to any disclaimer, the term of this patent is extended or adjusted under 35 U.S.C. 154(b) by 812 days.

This patent is subject to a terminal disclaimer.

(21) Appl. No.: 18/011,916

(22) PCT Filed: May 24, 2021

(86) PCT No.: PCT/IB2021/054479

§ 371 (c)(1),
(2) Date: Dec. 21, 2022

(87) PCT Pub. No.: WO2022/038424

PCT Pub. Date: Feb. 24, 2022

(65) Prior Publication Data

US 2023/0243840 A1 Aug. 3, 2023

(30) Foreign Application Priority Data

Aug. 20, 2020 (LV) ............................... P2020000056

(51) Int. Cl.
*G01N 33/58* (2006.01)
*G01N 33/68* (2006.01)
*G01N 33/92* (2006.01)

(52) U.S. Cl.
CPC ......... *G01N 33/582* (2013.01); *G01N 33/683* (2013.01); *G01N 33/92* (2013.01); *G01N 2405/04* (2013.01)

(58) Field of Classification Search
CPC ............. G01N 2405/04; G01N 33/582; G01N 33/683; G01N 33/92
See application file for complete search history.

(56) References Cited

U.S. PATENT DOCUMENTS

2023/0013542 A1* 1/2023 Arsenjans ............ G01N 33/582

FOREIGN PATENT DOCUMENTS

WO WO 2021105780 6/2021
WO WO 2022038424 2/2022

OTHER PUBLICATIONS

Dimitrijevs et al., "Cardiolipin in the spotlight: quantitative analysis and fluorescence-based competitive binding assay," Sens. Actuators B, 2021, vol. 346, 130537, pp. 1-8.*
International Search Report and Written Opinion in International Appln No. PCT/IB2020/058457, mailed on Dec. 9, 2020, 8 pages.
Kaewsuya et al., "Comparison of N-alkyl acridine orange dyes as fluorescence probes for the determination of cardiolipin," Analytical Chimica Acta, Sep. 2008, 626(2):111-118.
Kaewsuya et al., "Fluorescent determination of cardiolipin using 10-N-nonyl acridine orange 11," Analytical and Bioanalytical Chemistry, Feb. 2007, 387(8):2775-2782.
Mather et al., "Polycations induce the release of soluble intermembrane mitochondrial proteins," Biochem Biophys Acta, Sep. 2000, 1503(2001):357-368.
Nicolay et al., "The Interaction of Adriamycin with Cardiolipin in Model and Rat Liver Mitochondrial Membranes," Biochem Biophys Acta, Jun. 1984, 778(1984):359-371.
Parker et al., "Nuclear magnetic resonance study of doxorubicin binding to cardiolipin containing magnetically oriented phospholipid bilayers," Biochem Biophys Acta, Jun. 2001, 1514(2):206-216.
Sautrey et al., "Negatively-charged Lipids as Potential Target for New Amphiphilic Aminoglycoside Antibiotics: a biophysical study," J. Biological Chem., May 2016, M115.665364, 35 pages.
Sinibaldi et al., "Insights into Cytochrome c-Cardiolipin Interaction. Role Played by Ionic Strength," Biochemistry, Apr. 2008, 47(2008):6928-6935.
Soussi et al., "H-n.m.r. evaluation of the ferricytochrome c-cardiolipin interaction," Biochem. J., Aug. 1989, 265(1990):227-232.

* cited by examiner

*Primary Examiner* — Galina M. Yakovleva
(74) *Attorney, Agent, or Firm* — Fish & Richardson P.C.

(57) ABSTRACT

The present invention relates to a method for the evaluation of binding affinity of biologically active substances for cardiolipin based on acridinium salt utilization as a fluorescent probe.

13 Claims, 2 Drawing Sheets

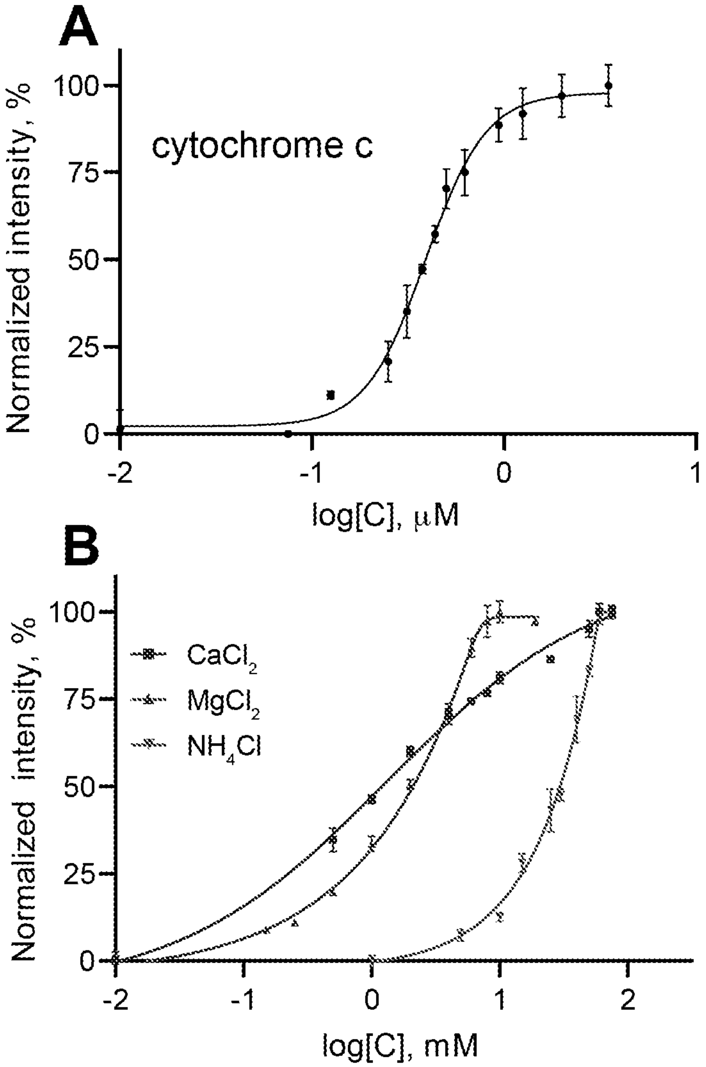
FIG.1 (1A, 1B)

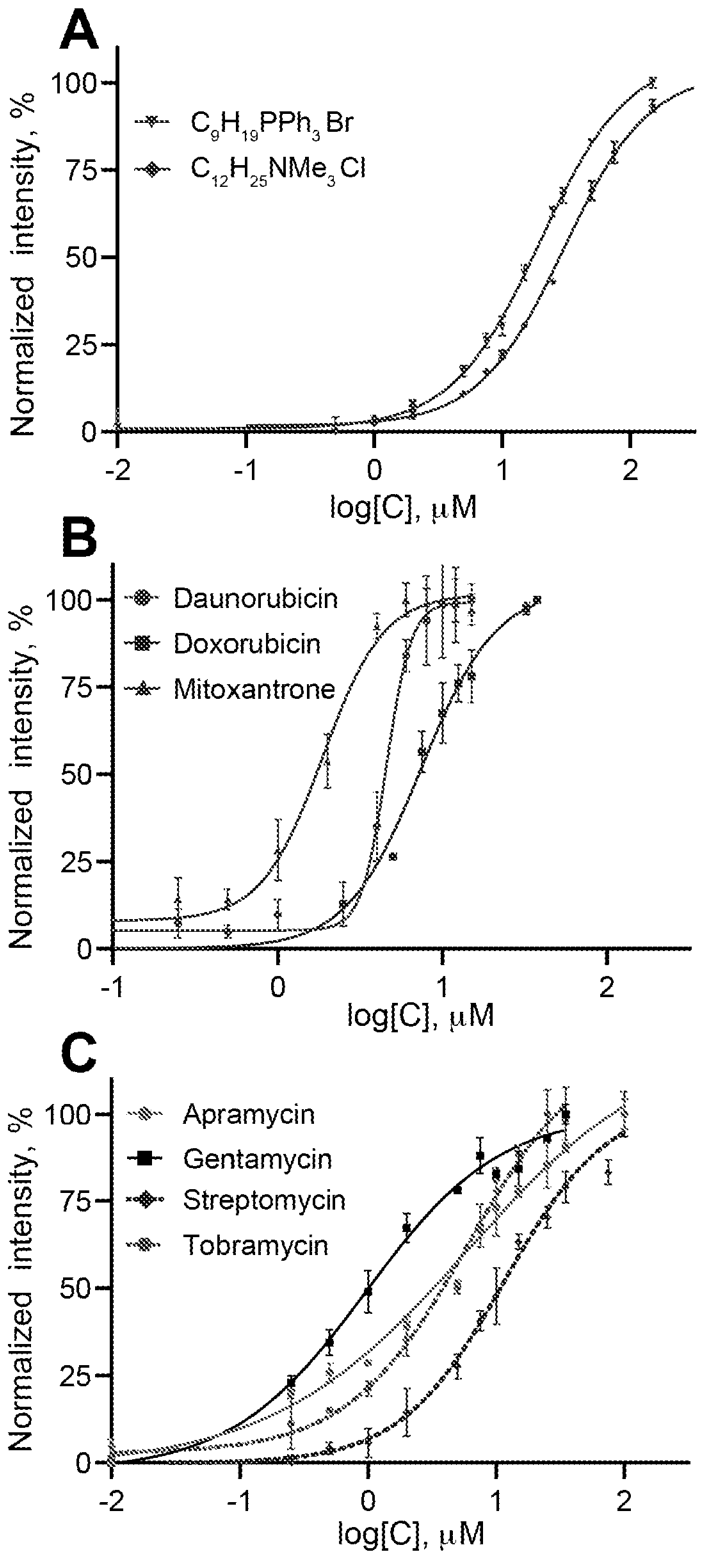
FIG.2 (2A,2B,2C)

ASSAY FOR MEASURING BINDING AFFINITY FOR CARDIOLIPIN OF BIOLOGICALLY ACTIVE COMPOUNDS

CROSS REFERENCE TO RELATED APPLICATIONS

This application is a U.S. national phase filing under 35 U.S.C. § 371 of International Application No. PCT/IB2021/054479, filed May 24, 2021, which claims priority to Latvian Application No. LVP2020000056, filed Aug. 20, 2020. The International Application was published in English on Feb. 24, 2022 as WO 2022/038424 under PCT Article 21 (2). The contents of the prior applications are incorporated herein by reference in their entirety.

FIELD OF THE INVENTION

The invention relates to a method for the evaluation of binding affinity of biologically active substances with negatively charged membrane. In particular, the invention relates to the fluorescent acridinium salt utilization as a fluorescent probe for measuring binding affinity of organic or inorganic substances for cardiolipin.

BACKGROUND OF THE INVENTION

Cardiolipin (CL) is a unique phospholipid which is localized in the inner mitochondrial membrane (IMM) in eukaryotes and in the cytoplasmic membrane of prokaryotes. CL provides mitochondrial membrane stability, dynamics and is required for optimal activity of several mitochondrial membrane proteins (e.g. electron transport chain (ETC) complexes I, III, IV, ATP synthase, cytochrome c). [1] Also, CL stabilizes anaerobic respiratory complexes in bacteria. [2] Because of its distinctive structural properties and localization CL is an attractive pharmacological target for mitochondria specific therapies along with antibiotic treatment. [3-5] Moreover, mitochondrial toxicity of some drugs, e.g. anthracyclines and aminoglycosides, is attributed to their ability to interact with CL [6-8] leading to life-threatening side effects such as heart failure and decline of renal function. [9, 10]

Consequently, exploring binding with CL is crucial for screening new, CL-targeted modulators of mitochondrial functions and antibiotics, as well as for evaluating drugs' potential to cause mitochondrial toxicity by interacting with CL.

Previously, compounds binding with CL was detected by $^{1}H$ and $^{13}C$ NMR [11,12], but this method is time-consuming, semi quantitative and requires large amount of both compound of interest and CL. Also, $Ca^{2+}$ can be used as a probe for evaluating compounds binding with anionic lipids, [13] but this method has significant disadvantages: non-specific $Ca^{2+}$ binding to CL, lacking hydrophobic interaction with CL and requirement of $Ca^{2+}$ electrode.

Other methods are based on a compound's intrinsic properties and includes circular dichroism measurements [14] or separation and quantification of unbound ligand. [15]

Earlier, 10-N-nonyl acridine orange (NAO) has been used as a fluorescent probe for the evaluation of 3',6-dinonyl neamine binding to anionic phospholipids, [16] although NAO has significant drawbacks and, therefore, a limited use as a probe for competition assays—fluorescence intensity of NAO is relatively low and unstable due to low solubility in aqueous medium.

Therefore, there is a great demand for a robust method that would allow rapid compound screening for CL targeting as well as binding affinity quantitative characterization. Recently we claimed acridinium salts bearing azetidine fragments as fluorescent dyes superior to NAO in photoluminescence quantum yield, stability and solubility. [17]

THE PRESENT INVENTION

We have surprisingly determined that certain 3,6-di(azetidin-1-yl)-10-substituted-acridin-10-ium salts can be used as fluorescent probe for evaluating binding affinity of organic and inorganic substances for cardiolipin.

OBJECTS OF THE INVENTION

It is an object of the present invention to provide an assay, useful for characterization of binding affinity of organic and inorganic compounds for cardiolipin.

SUMMARY OF THE INVENTION

Aspects of the invention relate to the development of an assay for the quantification of interaction of biologically active compounds with negatively charged phospholipids. In particular, utilization of 3,6-di(azetidin-1-yl)-10-(3-(trimethylsilyl)propyl)acridin-10-ium iodide (I) as a fluorescent probe for the determination of binding affinity of organic and inorganic compounds for CL.

I

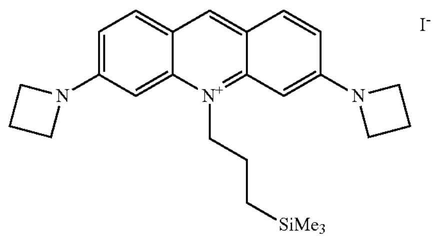

One aspect relates to the quantification of interaction of endogenous compounds (e.g. cytochrome c, calcium and magnesium ions) with CL. Another aspect of the invention relates to the exploring xenobiotics' ability to bind with CL (e.g. anthracyclins, anthracenediones, aminoglycosides, ammonium and phosphonium salts), which is an essential negatively charged phospholipid in the mitochondrial inner membrane and bacterial cytoplasmic membrane, based on fluorescent properties of compound I.

DETAILED DESCRIPTION OF THE INVENTION

Searching for the fluorescent probe for the determination of binding affinity of a series of organic and inorganic compounds with CL we unexpectedly discovered that 3,6-di(azetidin-1-yl)-10-(3-(trimethylsilyl)propyl)-acridin-10-ium iodide (I) exhibits appropriate properties. Our finding is astonishing, because there is no any fluorescence-based assay on the market that allows describing binding of compounds with CL.

We state that the described assay allows determining binding affinity of compounds of interest towards CL, which is incorporated into lipid vesicles membrane. This method has significant advantages over previously used methods: it allows quantitative characterization of binding with CL, it uses CL in a membrane (lipid vesicles) model that resembles natural membranes, reaction conditions (buffer, pH, temperature) may be flexibly modified, assay is relatively fast and simple, therefore is suitable for screening large number of compounds.

This method is excellent for exploring mitochondria-targeted, especially CL-targeted compounds, antibiotics, as well as predicting drugs' possible mitochondrial toxicity.

Description of the Assay:

Lipid vesicles may be composed of CL and a helper phospholipid (preferentially a phosphatidylcholine) or may have a more complex composition with several phospholipids, provided that the formulation is stable in the used medium. CL content may range from 0.5 mol % to 50 mol % of total phospholipids in a liposomal formulation, thereby covering CL content occurring in natural membranes. [18]

Assay might be carried out in various buffer solutions, e.g. HEPES (4-(2-hydroxyethyl)-1-piperazineethanesulfonic acid, CAS Nr. 7365-45-9, >99%), TRIS (tris(hydroxymethyl)aminomethane), MES (2-(N-morpholino)ethanesulfonic acid, CAS Nr. 4432-31-9, >99%), ADA (2-[(2-amino-2-oxoethyl)-(carboxymethyl)amino]acetic acid, CAS Nr. 26239-55-4, >99%) at pH ranging from 6.0 to 8.0.

Final concentration of the fluorescent probe I may range from 0.2 μM to 25 μM. Optimal incubation temperature is 37° C. because it represents physiological temperature and allows shortening of the incubation time. Compounds' incubation with CL containing liposomes may be varied from 10 min to 1 h.

Required Materials:

A fluorimeter is required that is capable of scanning emission intensity at a desired wavelength, as well as a plate shaker-thermostat. Assay is carried out in 96-well microplates for fluorescence-based assays. All buffers should be prepared from the highest-quality reagents and ultrapure water (MilliQ, 18.2 MΩ·cm$^{-1}$ at 25° C.) In this assay 20 mM HEPES solution is used, adjusting pH to 7.4 with aqueous 0.1 M NaOH solution. In the assay compound I stock solution in ethanol or DMSO (dimethyl sulfoxide) and stock solution of CL containing lipid vesicles in 20 mM HEPES buffer as well as ligand's stock solutions either in 20 mM HEPES buffer, ethanol or DMSO are used.

Representative Experimental Protocol:

Prior using the assay in a different buffer and pH it is advisable to perform CL containing liposomes titration with I (purity >95%) in order to find optimal CL:I molar ratio.

1. Prepare stock solution of I, stock solution of CL containing lipid vesicles and a stock solution of the ligand in 20 mM HEPES buffer.
2. In a 96-well microplate place CL containing lipid vesicles stock solution (CL final concentration 2.5 μM), then titrate it with a stock solution of a ligand and mix gently with a micro pipette by sucking the solution gently up and down (approximately 5 times). Also place a triplicate of CL containing lipid vesicles without a ligand (vehicle);
3. Place the 96-well microplate in a plate shaker-thermostat for 10 min (500 RPM, 37° C.).
4. Add appropriate amount of I stock solution (I final concentration 5 μM) to the wells, including wells containing vehicle, and mix gently with a micro pipette by sucking the solution gently up and down (approximately 5 times);
5. Incubate for 15 min in a plate shaker-thermostat (500 RPM, 37° C.);
6. Measure fluorescence intensity at an excitation and emission wavelength of 497 and 529 nm, respectively;
7. Normalize obtained fluorescence intensity (0%—CL liposomes with I without the ligand (vehicle), 100%—maximal effect of the ligand);
8. Plot the normalized fluorescence intensity against the concentration of the ligand on a logarithmic scale;
9. Fit the titration curve with a suitable fitting model to calculate $EC_{50}$ values.

EXAMPLES

There are listed representative examples of dose-effect curves obtained by the assay below. This method allows studying binding affinities for CL of small proteins, e.g. cytochrome c, inorganic cations, e.g. $Ca^{2+}$, $Mg^{2+}$, $NH_4^+$, as well as different xenobiotics such as aminoglycosides, anthracyclines, anthracenediones, ammonium and phosphonium cations.

Example 1. Cytochrome c from equine heart, Sigma-Aldrich, CAS Nr. 9007-43-6;

Example 2. Ammonium chloride for molecular biology, suitable for cell culture, >99.5%, Sigma-Aldrich, CAS Nr. 12125-02-9;

Example 3. Calcium chloride anhydrous, BioReagent, suitable for insect cell culture, suitable for plant cell culture, ≥96.0%, Sigma-Aldrich, CAS Nr. 10043-52-4;

Example 4. Magnesium chloride anhydrous, ≥98%, Sigma-Aldrich, CAS Nr. 7786-30-3;

Example 5. Doxorubicin hydrochloride, (8S,10S)-10-(((2R,4S,5R,6S)-4-amino-5-hydroxy-6-methyltetrahydro-2H-pyran-2-yl)oxy)-6,8,11-trihydroxy-8-(2-hydroxyacetyl)-1-methoxy-7,8,9,10-tetrahydrotetracene-5,12-dione hydrochloride, >95%, Fluorochem, CAS Nr. 25316-40-9;

Example 6. Daunorubicin hydrochloride, (8S,10S)-8-acetyl-10-(((2R,4S,5S,6S)-4-amino-5-hydroxy-6-methyltetrahydro-2H-pyran-2-yl)oxy)-6,8,11-trihydroxy-1-methoxy-7,8,9,10-tetrahydrotetracene-5,12-dione hydrochloride, >98.0%, Tokyo Chemical Industry, CAS Nr. 23541-50-6;

Example 7. Mitoxantrone dihydrochloride, 1,4-dihydroxy-5,8-bis((2-((2-hydroxyethyl)amino)ethyl)amino)anthracene-9,10-dione dihydrochloride, >97.0%, Tokyo Chemical Industry, CAS Nr. 70476-82-3;

Example 8. Gentamycin Sulfate, (2R,3S,4R,5R)-2-(((1S,2R,3R,4S,6R)-4,6-diamino (((2R,3R,6S)-3-amino-6-(1-(methylamino)ethyl)tetrahydro-2H-pyran-2-yl)oxy)-2-hydroxycyclohexyl)oxy)-5-methyl-4-(methylamino) tetrahydro-2H-pyran-3,5-diol sulfate, USP Grade, Fluorochem, CAS Nr. 1405-41-0;

Example 9. Apramycin sulfate salt, (2R,3R,4S,5S,6S)-5-amino (((2R,3S,4R,4aR,6S,7R,8aS)-7-amino-6-(((1R,2R,3S,4R,6S)-4,6-diamino-2,3-dihydroxycyclohexyl)oxy)-4-hydroxy-3-(methylamino)octahydropyrano[3,2-b]pyran-2-yl)oxy)-6-(hydroxymethyl)tetrahydro-2H-pyran-3,4-diol sulfate, Sigma-Aldrich, CAS Nr. 65710-07-8;

Example 10. Streptomycin Sulfate for Protein Research, 2-[(1R,2R,3S,4R,5R,6S)-3-(diaminomethyldeneamino)-4-[(2R,3R,4R,5S)-3-[(2S,3S,4S,5R,6S)-4,5-dihydroxy-6-(hydroxymethyl)-3-(methylamino)oxan-2-yl]oxy-4-formyl-4-hydroxy-5-methyloxolan-2-yl]oxy-2,5,6-trihydroxycyclohexyl]guanidine, >95.0%, Tokyo Chemical Industry, CAS Nr. 3810-74-0;

Example 11. Kanamycin sulfate from *Streptomyces kanamyceticus*, powder, BioReagent, suitable for cell culture, suitable for plant cell culture, 2-(aminomethyl)-6-[4,6-diamino-3-[4-amino-3,5-dihydroxy-6-(hydroxymethyl)

oxan-2-yl]oxy-2-hydroxycyclohexyl]-oxyoxane-3,4,5-triol sulfate, Sigma-Aldrich, CAS Nr. 25389-94-0;

Example 12. Tobramycin, (2S,3R,4S,5S,6R)-4-amino-2-{[(1S,2S,3R,4S,6R)-4,6-diamino-3-{[(2R,3R,5S,6R)-3-amino-6-(aminomethyl)-5-hydroxyoxan-2-yl]oxy}-2-hydroxycyclohexyl]oxy}-6-(hydroxymethyl)oxane-3,5-diol, Sigma-Aldrich, CAS Nr. 32986-56-4;

Example 13. Nonyltriphenylphosphonium bromide, >97.0%, CAS Nr. 60902-45-6. Prepared by the treatment of triphenyl phosphine with 1-bromononane in toluene according to [19].

Example 14. Dodecyltrimethylammonium chloride purum, ≥98.0% anhydrous basis, Sigma-Aldrich, CAS Nr. 112-00-5.

BRIEF DESCRIPTION OF THE DRAWINGS

FIG. 1 represents concentration-effect curves obtained in the competition binding assay of endogenous CL ligands—cytochrome c (A) and monovalent and bivalent cations (B) using CL-DOPC liposomes (25:75 mol %) and I as the CL-specific fluorescent probe.

FIG. 1A depicts cytochrome c binding with CL in 20 mM HEPES buffer at pH 7.4, using 2.5 μM CL and 5 μM I as a fluorescent probe. Particularly, normalized fluorescence intensity of I is plotted against various cytochrome c concentrations on a logarithmic scale and fit with four parameter logistic (4PL) curve allowing calculating $EC_{50}$ value.

FIG. 1B depicts $Ca^{2+}$, $Mg^{2+}$ and $NH_4^+$ binding with CL in 20 mM HEPES buffer at pH 7.4, using 2.5 μM CL and 5 μM I as a fluorescent probe Particularly, normalized fluorescence intensity of I is plotted against various $Ca^{2+}$, $Mg^{2+}$ and $NH_4^+$ concentrations on a logarithmic scale and fit with four parameter logistic (4PL) or five parameter logistic (5PL) curve allowing calculating $EC_{50}$ values. Under the same experimental conditions obtained $EC_{50}$ can be compared and related to the compounds' affinity for CL. Herein, $Ca^{2+}$, has ≈30% lower $EC_{50}$ than $Mg^{2+}$ and, therefore, higher affinity for CL. In turn, monovalent $NH_4^+$ ions have 23-fold lower affinity for CL than $Ca^{2+}$ ions.

FIG. 2 represents concentration-effect curve obtained in the competition binding assay of xenobiotics—mitochondria-targeted nonyltriphenylphosphonium bromide and dodecyltrimethylammonium chloride (A), anthracyclines and anthracenedione (B), and aminoglycosides (C) for CL using CL-DOPC liposomes (25:75 mol %) and I as the CL-specific fluorescent probe.

FIG. 2A depicts nonyltriphenylphosphonium bromide and dodecyltrimethylammonium chloride binding with CL in 20 mM HEPES buffer at pH 7.4, using 2.5 μM CL and 5 μM I as a fluorescent probe. Particularly, normalized fluorescence intensity of I is plotted against various nonyltriphenylphosphonium bromide and dodecyltrimethylammonium chloride concentrations on a logarithmic scale and fit with four parameter logistic (4PL) curve allowing calculating $EC_{50}$ values. Under these conditions nonyltriphenylphosphonium bromide's affinity for CL is ≈30% higher than that of dodecyltrimethylammonium chloride.

FIG. 2B shows daunorubicin, doxorubicin and mitoxantrone binding with CL in 20 mM HEPES buffer at pH 7.4, using 2.5 μM CL and 5 μM I as a fluorescent probe. Particularly, normalized fluorescence intensity of I is plotted against various daunorubicin, doxorubicin and mitoxantrone concentrations on a logarithmic scale and fit with four parameter logistic (4PL) curve allowing calculating $EC_{50}$ values. Mitoxantrone has the highest affinity for CL in this set of compounds, with twice as low $EC_{50}$ value compared to daunorubicin and thrice as low $EC_{50}$ value compared to doxorubicin.

FIG. 2C shows apramycin, gentamycin, streptomycin and tobramycin binding with CL in 20 mM HEPES buffer at pH 7.4, using 2.5 μM CL and 5 μM I as a fluorescent probe. Particularly, normalized fluorescence intensity of I is plotted against various daunorubicin, doxorubicin and mitoxantrone concentrations on a logarithmic scale and fit with four parameter logistic (4PL) or five parameter logistic (5PL) curve allowing calculating $EC_{50}$ Gentamicin has the highest affinity for CL in this series of aminoglycosides and the highest affinity among this set of xenobiotics, although gentamycin exhibits ≈3 times lower affinity toward CL than it's natural ligand cytochrome c. In turn, streptomycin has the lowest affinity for CL among studied aminoglycosides.

Table 1. lists $EC_{50}$ values obtained by the competition binding assay in 20 mM HEPES buffer at pH 7.4 (physiological pH) and 6.8 (pH of the intermembrane space in mitochondria [20]) using 2.5 μM CL and 5 μM I as a fluorescent probe. Among studied compounds cytochrome c, a natural CL ligand, exhibited the lowest $EC_{50}$ value, thus the highest binding affinity for CL. Inorganic cations showed much higher $EC_{50}$ values (in mM range). Mitoxantrone has $EC_{50}$ values in micromolar range and higher affinity for CL than doxorubicin and daunorubicin.

All studied aminoglycosides bind with CL but with different affinities—gentamicin exhibiting the highest and streptomycin exhibiting the lowest affinity toward CL. Mitochondria targeted nonyltriphenylphosphonium bromide and dodecyltrimethylammonium chloride have $EC_{50}$ values in micromolar range although lower affinities than studied aminoglycosides or anthracyclines. Nonyltriphenylphosphonium bromide and dodecyltrimethylammonium chloride were the only compounds studied whose interaction with CL was affected by changes of pH.

TABLE 1

$EC_{50}$ values obtained from competitive binding assay

| Example | Compound | $EC_{50}$ ± SD, μM pH = 7.4 | $EC_{50}$ ± SD, μM pH = 6.8 |
|---|---|---|---|
| 1 | Cytochrome C | 0.32 ± 0.06 | 0.28 ± 0.02 |
| 2 | $NH_4Cl$ | 31853.33 ± 2.30 | n.t.* |
| 3 | $CaCl_2$ | 1334.33 ± 10.10 | 1285.67 ± 129.5 |
| 4 | $MgCl_2$ | 1932.33 ± 20.51 | n.t. |
| 5 | Doxorubicin | 6.94 ± 0.90 | 5.86 ± 0.25 |
| 6 | Daunorubicin | 4.35 ± 1.25 | n.t. |
| 7 | Mitoxantrone | 2.04 ± 0.30 | n.t. |
| 8 | Gentamycin sulfate | 0.98 ± 0.14 | 1.01 ± 0.12 |

TABLE 1-continued

EC$_{50}$ values obtained from competitive binding assay

| Example | Compound | EC$_{50}$ ± SD, μM pH = 7.4 | pH = 6.8 |
|---|---|---|---|
| 9 | Apramycin sulfate | 3.34 ± 0.95 | n.t. |
| 10 | Streptomycin sulfate | 9.82 ± 1.76 | n.t. |
| 11 | Kanamycin sulfate | 4.32 ± 1.85 | n.t. |
| 12 | Tobramycin | 4.37 ± 0.32 | n.t. |
| 13 | Nonyltriphenylphosphonium bromide | 19.76 ± 0.75 | 36.65 ± 2.93 |
| 14 | Dodecyltrimethylammonium chloride | 30.71 ± 2.75 | 74.41 ± 8.47 |

Values are shown as the means ± S.D. from 3 independent experiments.
*n.t. - not tested.

Those values and binding curves were particularly encouraging, bearing in mind that developed assay allows studying and comparing organic and inorganic compound affinity for cardiolipin.

While the invention has been described with respect to certain embodiments, the description is intended to be exemplary, rather than limiting. Modifications and changes may be made within the scope of the invention, which is defined in the appended claims.

The invented procedure can be used for determination of substances' binding affinity for cardiolipin using a fluorescent probe e.g. compound I in an assay kit.

Wherein an assay kit comprising: fluorescent probe, appropriate buffer, cardiolipin containing material for the determination of organic and inorganic compounds binding to cardiolipin.

REFERENCES

[1] Paradies G, Paradies V, Ruggiero F M, Petrosillo G. Role of Cardiolipin in Mitochondrial Function and Dynamics in Health and Disease: Molecular and Pharmacological Aspects. Cells 2019; 8:728. doi:10.3390/cells8070728.

[2] Arias-Cartin R, Grimaldi S, Arnoux P, Guigliarelli B, Magalon A. Cardiolipin binding in bacterial respiratory complexes: Structural and functional implications. Biochim Biophys Acta—Bioenerg 2012; 1817:1937-49. doi:10.1016/j.bbabio.2012.04.005.

[3] El Khoury M, Swain J, Sautrey G, Zimmermann L, Van Der Smissen P, Décout J L, et al. Targeting Bacterial Cardiolipin Enriched Microdomains: An Antimicrobial Strategy Used by Amphiphilic Aminoglycoside Antibiotics. Sci Rep 2017; 7:1-12. doi:10.1038/s41598-017-10543-3.

[4] Tate A D, Antonelli P J, Hannabass K R, Dirain C O. Mitochondria-Targeted Antioxidant Mitoquinone Reduces Cisplatin-Induced Ototoxicity in Guinea Pigs. Otolaryngol—Head Neck Surg (United States) 2017; 156: 543-8. doi:10.1177/0194599816678381.

[5] Domenech O, Francius G, Tulkens P M, Van Bambeke F, Dufrêne Y, Mingeot-Leclercq M P. Interactions of oritavancin, a new lipoglycopeptide derived from vancomycin, with phospholipid bilayers: Effect on membrane permeability and nanoscale lipid membrane organization. Biochim Biophys Acta—Biomembr 2009; 1788:1832-40. doi:10.1016/j.bbamem.2009.05.003.

[6] Schwartz H S, Kanter P M. Chemical interactions of cardiolipin with daunorubicin and other intercalating agents. Eur J Cancer 1979; 15:923-8. doi:10.1016/0014-2964(79)90235-4.

[7] Maciel E, Domingues P, Marques D, Simões C, Reis A, Oliveira M M, et al. Cardiolipin and oxidative stress: Identification of new short chain oxidation products of cardiolipin in in vitro analysis and in nephrotoxic drug-induced disturbances in rat kidney tissue. Int J Mass Spectrom 2011; 301:62-73. doi:10.1016/j.ijms.2010.06.036.

[8] Kovacs E, Savopol T, Iordache M M, Săplăcan L, Sobaru I, Istrate C, et al. Interaction of gentamicin polycation with model and cell membranes. Bioelectrochemistry 2012; 87:230-5. doi:10.1016/j.bioelechem.2012.03.001.

[9] Geisberg C, Sawyer D B. Mechanisms of Anthracycline Cardiotoxicity and Strategies to Decrease Cardiac Damage Carrie. Curr Hypertens Rep 2010; 12:404-10. doi:10.1038/jid.2014.371.

[10] Santos N A G, Catão C S, Martins N M, Curti C, Bianchi M L P, Santos A C. Cisplatin-induced nephrotoxicity is associated with oxidative stress, redox state unbalance, impairment of energetic metabolism and apoptosis in rat kidney mitochondria. Arch Toxicol 2007; 81:495-504. doi:10.1007/s00204-006-0173-2.

[11] Parker M A, King V, Howard K P. Nuclear magnetic resonance study of doxorubicin binding to cardiolipin containing magnetically oriented phospholipid bilayers. Biochim Biophys Acta—Biomembr 2001; 1514:206-16. doi:10.1016/50005-2736(01)00371-6.

[12] Bassam Soussi, Ann-Christin Bylund-Fellenius, Tore Schersten J A. 'H-n.m.r. evaluation of the ferricytochrome c-cardiolipin interaction. Biochem J 1990; 265:227-32.

[13] Mather M, Rottenberg H. Polycations induce the release of soluble intermembrane mitochondrial proteins. Biochim Biophys Acta—Bioenerg 2001; 1503:357-68. doi:10.1016/S0005-2728(00)00231-0.

[14] Sinibaldi F, Fiorucci L, Patriarca A, Lauceri R, Ferri T, Coletta M, et al. Insights into cytochrome c-cardiolipin interaction. Role played by ionic strength. Biochemistry 2008; 47:6928-35. doi:10.1021/bi800048v.

[15] Nicolay K, Timmers R J M, Spoelstra E, Neut R Van Der, Fok J J, Huigen Y M, et al. The interaction of adriamycin with cardiolipin in model and rat liver mitochondrial membranes. BBA—Biomembr 1984; 778:359-71. doi:10.1016/0005-2736(84)90380-8.

[16] Sautrey G, El Khoury M, Giro Dos Santos A, Zimmermann L, Deleu M, Lins L, et al. Negatively charged lipids as a potential target for new amphiphilic aminoglycoside antibiotics: A biophysical study. J Biol Chem 2016; 291: 13864-74. doi:10.1074/jbc.M115.665364.

[17] Dimitrijevs P, Arsenjans P. Fluorescent acridinium salts, synthesis thereof and use for detection of cardiolipin. P-19-64, filled 28 Nov. 2019.

[18] Horvath S E, Daum G. Lipids of mitochondria. Prog Lipid Res 2013; 52:590-614. doi:10.1016/j.plipres.2013.07.002.

[19] Mostyn S N, Carland J E, Shimmon S, Ryan R M, Rawling T, Vandenberg R J. Synthesis and Characterization of Novel Acyl-Glycine Inhibitors of GlyT2. ACS Chem Neurosci 2017; 8:1949-59. doi:10.1021/acschemneuro.7b00105.

[20] Santo-Domingo J, Demaurex N. The renaissance of mitochondrial pH. J Gen Physiol 2012; 139:415-23. doi: 10.1085/jgp.201110767.

The invention claimed is:

1. An assay method, comprising:

incubating a solution comprising a compound of interest, a lipid vesicle containing cardiolipin, and 3,6-di(azetidin-1-yl)-10-(3-(trimethylsilyl)propyl)acridin-10-ium iodide (I)

(I)

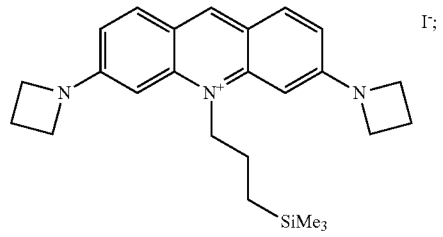

measuring fluorescence intensity at an excitation wavelength of 497 nm and at an emission wavelength of 529 nm, respectively.

2. The method of claim 1, wherein the compound of interest is an endogenous compound.

3. The method of claim 1, wherein the compound of interest comprises a metal cation.

4. The method of claim 1, wherein the compound of interest is an xenobiotic.

5. The method of claim 1, wherein the compound of interest comprises an ammonium or phosphonium cation.

6. The method of claim 1, wherein the compound of interest is an anthracycline or anthracenedione.

7. The method of claim 1, wherein the compound of interest is an aminoglycoside.

8. The method of claim 1, wherein the solution further comprises a buffer.

9. The method of claim 1, wherein 3,6-di(azetidin-1-yl)-10-(3-(trimethylsilyl)propyl)acridin-10-ium iodide is in a concentration of from 0.2 μM to 25 μM in the solution.

10. The method of claim 1, wherein the solution is incubated at 37° C.

11. The method of claim 1, further comprising determining an $EC_{50}$ value of the compound of interest after the measuring step.

12. The method of claim 1, wherein, before the incubating step, the method further comprises:

mixing the compound of interest and a lipid vesicle containing cardiolipin to form an intermediate solution;

incubating the intermediate solution; and adding 3,6-di(azetidin-1-yl)-10-(3-(trimethylsilyl)propyl)acridin-10-ium iodide into the intermediate solution.

13. A kit comprising:

3,6-di(azetidin-1-yl)-10-(3-(trimethylsilyl)propyl)acridin-10-ium iodide;

a buffer; and a material containing cardiolipin.

* * * * *